United States Patent
Yoshimura et al.

(10) Patent No.: US 8,865,938 B2
(45) Date of Patent: Oct. 21, 2014

(54) METHOD FOR PRODUCING BIS(AMINOMETHYL)CYCLOHEXANES

(75) Inventors: Naritoshi Yoshimura, Funabashi (JP); Shinji Kiyono, Kimitsu (JP); Tetsuya Hamada, Ichihara (JP); Eiji Watanabe, Chiba (JP); Saiko Sawada, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 13/877,595

(22) PCT Filed: Oct. 5, 2011

(86) PCT No.: PCT/JP2011/073004
§ 371 (c)(1),
(2), (4) Date: Apr. 3, 2013

(87) PCT Pub. No.: WO2012/046781
PCT Pub. Date: Apr. 12, 2012

(65) Prior Publication Data
US 2013/0197269 A1    Aug. 1, 2013

(30) Foreign Application Priority Data
Oct. 7, 2010   (JP) ................................. 2010-227745

(51) Int. Cl.
C07C 209/00 (2006.01)
C07C 209/48 (2006.01)
C07C 253/22 (2006.01)

(52) U.S. Cl.
CPC ........... *C07C 209/48* (2013.01); *C07C 2101/14* (2013.01); *C07C 253/22* (2013.01)
USPC ............ 564/448; 564/449; 564/450; 564/451

(58) Field of Classification Search
None
See application file for complete search history.

(56) References Cited

U.S. PATENT DOCUMENTS

| | | | |
|---|---|---|---|
| 2,888,484 A | 5/1959 | Dehm | |
| 3,296,293 A | 1/1967 | Strickland et al. | |
| 3,377,374 A | 4/1968 | Chapman et al. | |
| 3,998,881 A | 12/1976 | Butte, Jr. et al. | |
| 5,741,928 A | 4/1998 | Kobayashi et al. | |
| 2005/0014973 A1 | 1/2005 | Endou et al. | |
| 2008/0051600 A1 | 2/2008 | Endou et al. | |

FOREIGN PATENT DOCUMENTS

| | | |
|---|---|---|
| FR | 1420628 | 12/1965 |
| JP | 41-21338 B1 | 12/1966 |
| JP | 51-68540 | 6/1976 |
| JP | 60-224665 | 11/1985 |
| JP | 60-233045 | 11/1985 |
| JP | 63-010752 | 1/1988 |
| JP | 02-202856 | 8/1990 |
| JP | 8-143514 | 6/1996 |
| JP | 2001-187765 | 7/2001 |
| JP | 2003-026638 | 1/2003 |
| JP | 2010-163439 | 7/2010 |
| JP | 2011-006382 | 1/2011 |

OTHER PUBLICATIONS

Maegawa et al, European Journal of Chemistry-A, 2009, 15(28), 6953-6963.*
International Search Report PCT/JP2011/073004 dated Dec. 13, 2011.
R. Malachowski et al., Berichte Der Deutschen Chemischen Gesellschaft, vol. 71, No. 4, pp. 759-767, 1938.
Communication (Supplementary EP Search Report) in EP Appln No. 11830713.1 dated Feb. 5, 2014.
Maegawa, et al. "Efficient and Practical Arene Hydrogenation by Heterogeneous Catalysts under Mild Conditions", Chem. European Journal, 2009, vol. 15, pp. 6953-6963.
International Preliminary Report on Patentability issued in related International Patent Application No. PCT/JP2011/073004, dated May 16, 2013.

* cited by examiner

*Primary Examiner* — Sudhakar Katakam
(74) *Attorney, Agent, or Firm* — Foley & Lardner LLP

(57) ABSTRACT

A method for producing bis(aminomethyl)cyclohexanes includes a nuclear hydrogenation step of producing hydrogenated phthalic acids or phthalic acid derivatives by nuclear hydrogenation of phthalic acids or phthalic acid derivatives of at least one selected from the group consisting of phthalic acids, phthalic acid esters, and phthalic acid amides; a cyanation step of treating the hydrogenated phthalic acids or phthalic acid derivatives obtained in the nuclear hydrogenation step with ammonia, thereby producing dicyanocyclohexanes; and an aminomethylation step of treating the dicyanocyclohexanes obtained in the cyanation step with hydrogen, thereby producing bis(aminomethyl)cyclohexanes. In the cyanation step, metal oxide is used as a catalyst, and the obtained dicyanocyclohexanes have a metal content of 3000 ppm or less.

9 Claims, No Drawings

METHOD FOR PRODUCING BIS(AMINOMETHYL)CYCLOHEXANES

This application is a National Stage application of PCT application no. PCT/JP2011/073004 filed Oct. 5, 2011, which claims priority to Japanese patent application no. JP 2010/227,745 filed Oct. 7, 2010.

TECHNICAL FIELD

The present invention relates to a method for producing bis(aminomethyl)cyclohexanes.

BACKGROUND ART

Heretofore, bis(aminomethyl)cyclohexanes have been well known for a raw material of polyamide used for fiber, film, etc. Also, bis(isocyanatomethyl)cyclohexanes derived from bis(aminomethyl)cyclohexanes are useful as a raw material of polyurethane used for, for example, paints, adhesives, plastic lenses, etc.

As a method for producing such bis(aminomethyl)cyclohexanes, for example, Patent Document 1 below has proposed a method for producing bis(aminomethyl)cyclohexanes by nuclear hydrogenation (hydrogen addition to aromatic rings) of xylylenediamine in the presence of, for example, a ruthenium catalyst using one or more solvents selected from alkylamines and alkylenediamines.

As a method for producing xylylenediamine used in the above-described method, for example, Patent Document 2 has proposed ammoxidation of xylene using a metal oxide catalyst such as vanadium to produce phthalonitrile, and then hydrogenation of the phthalonitrile in the presence of a nickel catalyst.

Patent Document 3 below has proposed a method for producing bis(aminomethyl)cyclohexanes in which hydrogen cyanide is added to 4-cyanocyclohexene to produce dicyanocyclohexanes, and then the dicyanocyclohexanes are hydrogenated in the presence of a catalyst.

Furthermore, as a method for producing bis(aminomethyl)cyclohexane, for example, Non-Patent Document 1 (Malachowski et al.) discloses the following: an acid chloride derivative is prepared using cyclohexanedicarboxylic acid with thionyl chloride; cyclohexane diamide is prepared using the acid chloride derivative with ammonia; and thereafter, the cyclohexane diamide is further allowed to react with thionyl chloride to obtain dicyanocyclohexane, and then the obtained dicyanocyclohexane is hydrogenated.

CITATION LIST

Patent Document

Patent Document 1
Japanese Unexamined Patent Publication No. H8-143514
Patent Document 2
Japanese Unexamined Patent Publication No. 2003-26638
Patent Document 3
Japanese Unexamined Patent Publication No. H2-202856

Non-Patent Document

Non-Patent Document 1
Berichte Der Deutschen Chemischen Gesellschaft, vol. 71, No. 4, p 759 (1938)

SUMMARY OF THE INVENTION

Problem to be Solved by the Invention

However, when xylylenediamine is produced as a raw material of bis(aminomethyl)cyclohexanes by the method described in Patent Document 2, xylene has to be subjected to ammoxidation with a very high temperature of 420° C. to produce phthalonitrile, and thereafter, the obtained phthalonitrile has to be hydrogenated at a very high pressure of 12 MPa (Patent Document 2 above (ref: Example 1)).

Furthermore, when bis(aminomethyl)cyclohexane is produced by the method described in the above Patent Document 1 from the thus obtained xylylenediamine, nuclear hydrogenation of xylylenediamine at a very high pressure of 100 kg/cm$^2$ (10 MPa) has to be performed (ref: Patent Document 1 above (Reference Examples)).

Also, when dicyanocyclohexane, i.e., a raw material of bis(aminomethyl)cyclohexane is produced by the method described in Patent Document 3, hydrogen cyanide is added to 4-cyanocyclohexene, and hydrogen cyanide is highly poisonous, and its handling requires a great deal of care, thus being significantly disadvantageous for industrial use.

That is, with the methods described in the above-described Patent Documents 1 to 3, reaction of the components at high temperature and under high pressure may be required, and there may be disadvantages in terms of handleability, and thus improvement in facilities and safety has been demanded.

Also, the method described in Non-Patent Document 1 includes steps of multiple stages, and furthermore, requires use of a large amount of thionyl chloride, which is highly corrosive and thus hard to handle, and on top of that, the reaction yield in each of the steps is low.

Thus, in the method described in Non-Patent Document 1, in view of industrial production, improvements in terms of many aspects are desired.

The present invention was achieved in view of those disadvantages, and its object is to provide a method that is excellent in terms of equipment, safety, and economy for producing bis(aminomethyl)cyclohexanes.

Means for Solving the Problem

A method for producing bis(aminomethyl)cyclohexanes of the present invention includes:
  a nuclear hydrogenation step of producing hydrogenated phthalic acids or phthalic acid derivatives by nuclear hydrogenation of phthalic acids or phthalic acid derivatives,
    the phthalic acids or phthalic acid derivatives being at least one selected from the group consisting of phthalic acids, phthalic acid esters, and phthalic acid amides;
  a cyanation step of treating the hydrogenated phthalic acids or phthalic acid derivatives obtained in the nuclear hydrogenation step with ammonia to produce dicyanocyclohexanes; and
  an aminomethylation step of treating the dicyanocyclohexanes obtained in the cyanation step with hydrogen, thereby producing bis(aminomethyl)cyclohexanes;
  wherein metal oxide is used as a catalyst in the cyanation step, and the obtained dicyanocyclohexanes have a metal content of 3000 ppm or less.

A method for producing bis(aminomethyl)cyclohexanes of the present invention includes a cyanation step of treating hydrogenated phthalic acids or phthalic acid derivatives with ammonia, thereby producing dicyanocyclohexanes; and an aminomethylation step of treating the dicyanocyclohexanes obtained in the cyanation step with hydrogen, thereby producing bis(aminomethyl)cyclohexanes, wherein metal oxide is used as a catalyst in the cyanation step, and the obtained dicyanocyclohexanes have a metal content of 3000 ppm or less.

In the above-described production method, it is preferable that the hydrogenated phthalic acids or phthalic acid derivatives are obtained by a nuclear hydrogenation step of nuclear hydrogenation of phthalic acids or phthalic acid derivatives of at least one selected from the group consisting of phthalic acids, phthalic acid esters, and phthalic acid amides.

In the method for producing bis(aminomethyl)cyclohexanes of the present invention, it is preferable that in the cyanation step, the ammonia to be brought into contact with is fed at a rate greater than 0.5 mol equivalent/hydrogenated phthalic acids or phthalic acid derivatives/hr.

In the method for producing bis(aminomethyl)cyclohexanes of the present invention, it is preferable that in the cyanation step, the reaction with ammonia is performed in the presence of a solvent having a boiling point of 180° C. to 350° C.

In the method for producing bis(aminomethyl)cyclohexanes of the present invention, it is preferable that in the cyanation step, the reaction with ammonia is performed in the presence of 3 to 20 parts by weight of a solvent relative to 100 parts by weight the hydrogenated phthalic acids or phthalic acid derivatives.

In the method for producing bis(aminomethyl)cyclohexanes of the present invention, it is preferable that a solvent is used in the cyanation step, the solvent being selected from o-dichlorobenzene, triethylene glycol dim ethylether, tetraethylene glycol dimethylether, N-methyl-2-pyrrolidinone, N,N'-dimethylimidazolidinone, N,N'-diethylimidazolidinone, N,N'-dipropylimidazolidinone, N,N',4-trimethylimidazolidinone, and N,N'-dimethylpropyleneurea.

Effect of the Invention

The method for producing bis(aminomethyl)cyclohexanes of the present invention is excellent in terms of equipment, safety, and economy, and achieves safe, low costs, and high yield production of bis(aminomethyl)cyclohexanes. Thus, the present invention can be suitably used as an industrial method for producing bis(aminomethyl)cyclohexanes.

EMBODIMENT OF THE INVENTION

A method for producing bis(aminomethyl)cyclohexanes of the present invention includes
a nuclear hydrogenation step of producing hydrogenated phthalic acids or phthalic acid derivatives by nuclear hydrogenation of phthalic acids or phthalic acid derivatives,
the phthalic acids or phthalic acid derivatives being at least one selected from the group consisting of phthalic acids, phthalic acid esters, and phthalic acid amides;
a cyanation step of treating the hydrogenated phthalic acids or phthalic acid derivatives obtained in the nuclear hydrogenation step with ammonia to produce dicyanocyclohexanes; and
an aminomethylation step of treating the dicyanocyclohexanes obtained in the cyanation step with hydrogen, thereby producing bis(aminomethyl)cyclohexanes.

Each step is described in detail in the following.

[Nuclear Hydrogenation Step]

In the nuclear hydrogenation step, nuclear hydrogenation of phthalic acids or phthalic acid derivatives is performed, the phthalic acids or phthalic acid derivatives being at least one selected from the group consisting of phthalic acids, phthalic acid esters, and phthalic acid amides, to produce corresponding hydrogenated phthalic acids or phthalic acid derivatives (that is, hydrogenated phthalic acids or phthalic acid derivatives of at least one selected from the group consisting of cyclohexanedicarboxylic acids, cyclohexanedicarboxylic acid esters, and cyclohexanedicarboxylic acid amides).

Examples of phthalic acids include phthalic acid (ortho-phthalic acid), isophthalic acid (meta-phthalic acid), and terephthalic acid (para-phthalic acid).

These phthalic acids or phthalic acid derivatives may be used singly or in a combination of two or more.

The substituted positions of the functional groups on the cyclohexane ring of the hydrogenated phthalic acids or phthalic acid derivatives obtained in the nuclear hydrogenation step correlate with the ortho-, meta-, or para-form of the raw material component of phthalic acids or phthalic acid derivatives.

That is, for example, when isophthalic acid or an isophthalic acid derivative is used as the phthalic acids or phthalic acid derivatives, the hydrogenated phthalic acids or phthalic acid derivatives to be produced are hydrogenated phthalic acids or phthalic acid derivatives of at least one selected from the group consisting of cyclohexane-1,3-dicarboxylic acid, cyclohexane-1,3-dicarboxylic acid ester, and cyclohexane-1,3-dicarboxylic acid amide; and when terephthalic acid or a terephthalic acid derivative is used as the phthalic acids or phthalic acid derivatives, the hydrogenated phthalic acids or phthalic acid derivatives to be produced are hydrogenated phthalic acids or phthalic acid derivatives of at least one selected from the group consisting of cyclohexane-1,4-dicarboxylic acid, cyclohexane-1,4-dicarboxylic acid ester, and cyclohexane-1,4-dicarboxylic acid amide.

In the nuclear hydrogenation step, for example, the method described in Japanese Unexamined Patent Publication No. 2001-181223 may be used.

The phthalic acids or phthalic acid derivatives used as a raw material in the present invention may be one having quality of industrially available products, and also undried (containing water) phthalic acids or phthalic acid derivatives that have undergone the purification in the hydrogenation step generally performed in production of phthalic acids may be used.

The reaction in the nuclear hydrogenation step is exothermic reaction, and therefore to suitably suppress the temperature increase due to the heat of reaction, and also to increase conversion, it is preferable that a solvent that is inactive in such a reaction is added as a diluent to the raw material phthalic acids or phthalic acid derivatives for dilution so that the phthalic acid or phthalic acid derivative concentration in the reaction solution is, for example, 1 to 50 wt %, preferably 2 to 30 wt %. When the concentration in the reaction solution is within the range, it is advantageous in that the reaction rate is not reduced, and the temperature increase in the reactor is small.

Examples of such a solvent include aqueous solvents such as water, methanol, ethanol, 1-propanol, isopropanol, 1-butanol, 2-butanol, sec-butanol, t-butanol, and 1,4-dioxane.

Use of such an aqueous solvent is advantageous in that the reaction mixture in the nuclear hydrogenation step can be cooled as necessary, and recirculated for use.

In this case, water is used preferably because it can be recovered by separation operation thereafter; it does not allow unwanted components to be mixed into the reaction system; and undried phthalic acids that underwent the purification step of phthalic acids can be used.

In the nuclear hydrogenation step, hydrogen used in the nuclear hydrogenation may be of industrial use quality. For example, the hydrogen may contain inactive gas (e.g., nitrogen, methane, etc.) but its hydrogen concentration is preferably 50% or more.

The hydrogen amount is preferably about 3 to 50 times the raw material phthalic acids or phthalic acid derivatives in molar ratio.

When the hydrogen amount is within such a range, the amount of unreacted materials is small, the reaction rate is sufficient, and it is advantageous economically.

In the nuclear hydrogenation step, a known catalyst may be added.

The catalyst used in the nuclear hydrogenation step is a general use noble metal catalyst for nuclear hydrogenation. To be specific, examples of such a catalyst include palladium, platinum, ruthenium, and rhodium, and preferably, palladium or ruthenium is used.

These catalysts are preferably prepared as a supported catalyst. Examples of carriers for such catalysts include activated carbon, alumina, silica, and kieselguhr, and preferably, activated carbon or silica is used.

The amount of metal (e.g., palladium, platinum, ruthenium, rhodium, etc.) supported is in the range of, for example, 0.1 to 10 wt %, preferably 0.5 to 10 wt % of the total amount including the catalyst carrier.

When the amount of metal supported is within such a range, it is preferable because the activity of catalyst per weight is high.

The catalyst is used in the form of, for example, powder, granular, or may be supported on a pellet carrier. Preferably, the catalyst is in the form of powder. When the catalyst has an appropriate size, for example, when the catalyst is powder catalyst, the catalyst contains an internal portion that effectively contributes to reaction in a large amount, and therefore the reaction rate does not easily decrease.

The catalyst amount relative to 100 parts by weight of phthalic acids or phthalic acid derivatives is in the range of, for example, 0.1 to 50 parts by weight, preferably 0.5 to 20 parts by weight.

The phthalic acids or phthalic acid derivatives are not highly soluble in general solvents such as water, and therefore the reaction is preferably performed in a suspension of the raw material and the solvent.

The reactor is preferably a pressure-resistant vessel.

A raw material slurry and hydrogen are introduced from the reactor top or bottom, and brought into contact with the catalyst in a suspension. After the reaction, the product, i.e., hydrogenated phthalic acids or phthalic acid derivatives, is highly soluble in a general solvent such as water at high temperature, and therefore separation from the catalyst can be performed by filtration.

In the filtration, the above-described product is dissolved in, for example, a known alkaline solution (e.g., aqueous sodium hydroxide solution, etc.), and after the solution is filtered, the solution can be neutralized by a known acid solution (e.g., aqueous hydrogen chloride solution, etc.).

Thereafter, by drying or concentrating the mixture, or by crystallizing the product by cooling, hydrogenated phthalic acids or phthalic acid derivatives can be obtained.

The reaction temperature is usually in the range of 50 to 200° C., and preferably 100 to 160° C.

The reaction temperature within such a range is advantageous in that the amount of unreacted materials and by-products is less, hydrogenolysis does not occur easily, and as a result, the yield increases.

The reaction pressure is usually in the range of 0.5 to 15 MPa, preferably 2 to 15 MPa, more preferably 2 to 8 MPa, even more preferably 2 to 5 Mpa.

The reaction pressure within such a range is advantageous in that the reaction rate does not easily decrease, and the amount of by-products is less.

The conversion of phthalic acids or phthalic acid derivatives is usually 90% or more, preferably 95% or more, and more preferably 98% or more.

When the amount of the unreacted phthalic acids or phthalic acid derivatives is small as described above, it is advantageous in that after treatment such as separation and purification of the product from the reaction mixture become not so complicated.

The hydrogenated phthalic acids or phthalic acid derivatives obtained in the nuclear hydrogenation step have functional groups at substituted positions correlating with the ortho-, meta-, or para-form of the phthalic acids or phthalic acid derivatives used as the raw material, and are a mixture of cis isomer and trans isomer.

To be more specific, for example, when isophthalic acid or an isophthalic acid derivative (meta-phthalic acid) is used as the raw material, the hydrogenated phthalic acids or phthalic acid derivatives to be produced are a mixture of 1,3-disubstituted cis isomer (that is, cis-cyclohexane-1,3-dicarboxylic acid, cis-cyclohexane-1,3-dicarboxylic acid ester, and/or cis-cyclohexane-1,3-dicarboxylic acid amide), and 1,3-disubstituted trans isomer (that is, trans-cyclohexane-1,3-dicarboxylic acid, trans-cyclohexane-1,3-dicarboxylic acid ester, and/or trans-cyclohexane-1,3-dicarboxylic acid amide); and when terephthalic acid or a terephthalic acid derivative (para-phthalic acid) is used as the raw material, the hydrogenated phthalic acids or phthalic acid derivatives to be produced are a mixture of 1,4-disubstituted cis isomer (that is, cis-cyclohexane-1,4-dicarboxylic acid, cis-cyclohexane-1,4-dicarboxylic acid ester, and/or cis-cyclohexane-1,4-dicarboxylic acid amide), and 1,4-disubstituted trans isomer (that is, trans-cyclohexane-1,4-dicarboxylic acid, trans-cyclohexane-1,4-dicarboxylic acid ester, and/or trans-cyclohexane-1,4-dicarboxylic acid amide).

Furthermore, for example, when isophthalic acid or an isophthalic acid derivative (meta-phthalic acid), and terephthalic acid or a terephthalic acid derivative (para-phthalic acid) are used in combination as the raw materials, the hydrogenated phthalic acids or phthalic acid derivatives to be produced are a mixture of the above-described 1,3-disubstituted cis isomer, 1,3-disubstituted trans isomer, 1,4-disubstituted cis isomer, and 1,4-disubstituted trans isomer.

[Cyanation Step]

In the cyanation step, the above-described hydrogenated phthalic acids or phthalic acid derivatives obtained in the nuclear hydrogenation step are treated with ammonia to produce dicyanocyclohexanes.

In the cyanation step, for example, the method described in Japanese Unexamined Patent Publication No. S63-10752 may be used.

To be more specific, in the cyanation step, the hydrogenated phthalic acids or phthalic acid derivatives obtained in the nuclear hydrogenation step are allowed to react with a compound capable of serving as an ammonia source (e.g., ammonia, urea, ammonium carbonate, etc.)(hereinafter may be referred to as ammonia source) by heating at, usually 200° C. or more and below 350° C., preferably 230° C. or more and below 320° C.

The reaction temperature within such a range is advantageous in that the reaction rate does not decrease, and decomposition due to excessive heating occurs less.

In the present invention, metal oxide is used as a catalyst in the cyanation step.

Examples of metal oxide include silica, alumina, phosphorus pentoxide, tin oxide, titanium oxide, zinc oxide, iron oxide, zirconium oxide, and cobalt oxide.

Of these metal oxides, in view of easy separation after reaction, silica, alumina, tin oxide, titanium oxide, zinc oxide, iron oxide, zirconium oxide, or cobalt oxide is preferably used.

In this step, furthermore, metal oxide and other catalysts can be used in combination, and examples of such a catalyst include mineral acids such as hydrochloric acid, phosphoric acid, and sulfuric acid, and organic acids such as acetic acid, propionic acid, and benzoic acid.

When metal oxide and other catalyst are used in combination, the mixing ratio of these is not particularly limited, and is set suitably in accordance with the purpose and application.

The catalyst is used in the form of for example, powder, granular, or may be supported on a pellet carrier. Preferably, the catalyst is powder.

When the catalyst has an appropriate size, for example, when the catalyst is powder catalyst, the catalyst contains an internal portion that effectively contributes to reaction in a large amount, and therefore the reaction rate does not easily decrease.

The catalyst amount relative to 100 parts by weight of hydrogenated phthalic acids or phthalic acid derivatives is in the range of, for example, 0.1 to 50 parts by weight, preferably 0.5 to 20 parts by weight.

In the reaction, a solvent is preferably used as appropriate.

Examples of the solvent include, although any solvent that does not inhibit the purpose of the method of the present invention can be used, aliphatic or alicyclic hydrocarbons such as decane, undecane, dodecane, tridecane, tetradecane, pentadecane, and decalin; aromatic hydrocarbons such as mesitylene, tetralin, butylbenzene, p-cymene, diethylbenzene, diisopropylbenzene, triethylbenzene, cyclohexylbenzene, dipentylbenzene, and dodecylbenzene; alcohols such as hexanol, 2-ethylhexanol, octanol, decanol, dodecanol, ethylene glycol, diethylene glycol, and triethylene glycol; ethers such as diethylene glycol dimethylether, triethylene glycol dimethylether, tetraethylene glycol dimethylether, o-dimethoxybenzene, ethylphenylether, butylphenylether, and o-diethoxybenzene; halogenated aromatic hydrocarbons such as iodobenzene, o-dichlorobenzene, m-dichlorobenzene, 1,2,4-trichlorobenzene, o-dibromobenzene, bromochlorobenzene, o-chlorotoluene, p-chlorotoluene, p-chloroethylbenzene, and 1-chloronaphthalene; polar aprotic solvents such as dimethyl sulfoxide, N,N-dimethylformamide, N,N-dimethylacetamide, hexamethylphosphoramide, N-methyl-2-pyrrolidinone, N,N'-dimethylimidazolidinone, N,N'-diethylimidazolidinone, N,N-dipropylimidazolidinone, N,N',4-trimethylimidazolidinone, and N,N'-dimethylpropyleneurea; and the product in this step, i.e., 1,4-dicyanocyclohexane. These solvents may be used singly or in a combination of two or more.

As the solvent, in view of suppressing crystallization of dicyanocyclohexanes to the gas purge line of the reactor, and to apparatuses at downstream of the reactor such as a condenser, the solvent is preferably selected from, for example, ethers such as diethylene glycol dimethylether, triethylene glycol dimethylether, tetraethylene glycol dimethylether, o-dimethoxybenzene, ethylphenylether, butylphenylether, and o-diethoxybenzene; halogenated aromatic hydrocarbons such as iodobenzene, o-dichlorobenzene, m-dichlorobenzene, 1,2,4-trichlorobenzene, o-dibromobenzene, bromochlorobenzene, o-chlorotoluene, p-chlorotoluene, p-chloroethylbenzene, and 1-chloronaphthalene; and polar aprotic solvents such as dimethyl sulfoxide, N,N-dimethylformamide, N,N-dimethylacetamide, hexamethylphosphoramide, N-methyl-2-pyrrolidinone, N,N'-dimethylimidazolidinone, N,N'-diethylimidazolidinone, N,N'-dipropylimidazolidinone, N,N',4-trimethylimidazolidinone, and N,N'-dimethylpropyleneurea.

Of the above-described solvents, those solvents having a boiling point of 180° C. to 350° C. is preferably used. Use of the solvent having a boiling point of lower than 180° C. is not preferable because the energy load on the reactor increases. Use of the solvent having a boiling point higher than 350° C. is not preferable because the effects of suppressing the crystallization of dicyanocyclohexanes to the reactor gas purge line and to apparatuses at downstream of the reactor such as a condenser decreases.

In view of the above, of the above-described solvents, selection is made preferably from o-dichlorobenzene, triethylene glycol dimethylether, tetraethylene glycol dimethylether, polar aprotic solvents such as N-methyl-2-pyrrolidinone, N,N'-dimethylimidazolidinone, N,N'-diethylimidazolidinone, N,N'-dipropylimidazolidinone, N,N',4-trimethylimidazolidinone, and N,N'-dimethylpropyleneurea.

The amount of solvent used is not particularly limited, and usually is 10 times or less by weight the reactant (including the above-described hydrogenated phthalic acids or phthalic acid derivatives obtained in the nuclear hydrogenation step), preferably 1 time or less by weight the reactant, and more preferably 3 to 20 parts by weight relative to 100 parts by weight of the hydrogenated phthalic acids or phthalic acid derivatives. When the amount of the solvent is small, or when no solvent is used, suppression of crystallization of dicyanocyclohexanes to the gas purge line of the reactor and to apparatuses at downstream of the reactor such as a condenser becomes difficult, and when the amount of the solvent is large, it is not preferable because energy load on the reactor increases.

The reaction method is not particularly limited, and examples thereof include slurry-bed batch process, semi-batch process, and continuous process; and also fixed-bed continuous process. Preferably, liquid-phase slurry reaction is used.

The reactor is preferably a pressure-resistant vessel.

For example, hydrogenated phthalic acids or phthalic acid derivatives, and a catalyst are introduced from the reactor top or bottom, and the hydrogenated phthalic acids or phthalic acid derivatives are dissolved by heating to be suspended; and an ammonia source such as ammonia is fed intermittently or continuously to the reactor, to allow reaction at a predetermined temperature.

The amount of the ammonia source to be fed is, in view of making ammonia easy to treat or recover after reaction, for example, 1 to 20 mol, preferably 2 to 20 mol relative to 1 mol of hydrogenated phthalic acids or phthalic acid derivatives.

The rate of the feeding of the ammonia source is not particularly limited, and preferably 0.1 mol to 2 mol per 1 hour relative to 1 mol of hydrogenated phthalic acids or phthalic acid derivatives, and more preferably, more than 0.5 mol and 2 mol or less (that is, more than 0.5 mol equivalent/hydrogenated terephthalic acids or terephthalic acid derivatives/hr and 2 mol equivalent/hydrogenated terephthalic acids or terephthalic acid derivatives/hr or less). The feeding rate lower than 0.5 mol relative to 1 mol of hydrogenated phthalic acids or phthalic acid derivatives per 1 hour is not preferable because the reaction requires a long time. The feeding rate higher than 2 mol relative to 1 mol of hydrogenated phthalic acids or phthalic acid derivatives per 1 hour is disadvantageous economically in that the unreacted ammonia source increase in volume, and therefore, for example, when ammonia is to be recovered and reused, the burden is substantial.

The feeding time is suitably selected depending on the feeding rate. For example, the feeding time is 1 to 80 hours, preferably 2 to 50 hours.

Water is produced as a by-product in this reaction, and therefore in view of accelerating the reaction rate, water is preferably removed out of the system. To remove water out of the system, for example, an inactive gas such as nitrogen can be fed to the reactor.

The reaction may be performed under any pressure condition, for example, under elevated pressure, ambient pressure, and reduced pressure, which is suitably selected.

After the reaction, the product dicyanocyclohexanes are obtained as a mixture (mixture of stereoisomers) of the cis isomer and trans isomer.

The dicyanocyclohexanes obtained in the cyanation step have functional groups at substituted positions correlating with the ortho-, meta-, or para-form of the phthalic acids or phthalic acid derivatives used as the raw material, and are a mixture of cis isomer and trans isomer.

To be more specific, for example, when isophthalic acid or an isophthalic acid derivative is used as the raw material, dicyanocyclohexanes to be produced are a mixture of 1,3-disubstituted cis isomer (that is, cis-1,3-dicyanocyclohexane) and 1,3-disubstituted trans isomer (that is, trans-1,3-dicyanocyclohexane); and for example, when terephthalic acid or a terephthalic acid derivative (para-phthalic acid) is used as the raw material, dicyanocyclohexanes to be produced are a mixture of 1,4-disubstituted cis isomer (that is, cis-1,4-dicyanocyclohexane) and 1,4-disubstituted trans isomer (that is, trans-1,4-dicyanocyclohexane).

Furthermore, for example, when isophthalic acid or an isophthalic acid derivative (meta-phthalic acid) and terephthalic acid or a terephthalic acid derivative (para-phthalic acid) are used in combination as the raw materials, the dicyanocyclohexanes to be produced are a mixture of the above-described 1,3-disubstituted cis isomer, 1,3-disubstituted trans isomer, 1,4-disubstituted cis isomer, and 1,4-disubstituted trans isomer.

The cis isomer/trans isomer ratio of the dicyanocyclohexanes obtained converges to the equilibrium composition ratio of dicyanocyclohexanes at the reaction temperature, approximately, to cis isomer/trans isomer=40/60 to 60/40, regardless of the stereo isomer ratio of the hydrogenated phthalic acids or phthalic acid derivatives.

If necessary, from the stereo isomer mixture of the dicyanocyclohexanes after reaction, the catalyst used is removed by a known method, for example, such as filtering and adsorption, and thereafter, the cis and trans isomer can be separated from the mixture, for example, by fractional crystallization using the difference in their solubility, or by distillation using the difference in their boiling points.

For example, the solvent used in the fractional crystallization is preferably a solvent in which the solubility of the cis isomer and its of the trans isomer of dicyanocyclohexanes is greatly different, and examples thereof include water; lower fatty acids such as acetic acid; alcohols such as methanol, ethanol, 1-propanol, isopropanol, 1-butanol, 2-butanol, t-butanol, and ethylene glycol; and ethers such as diethylether and 1,4-dioxane.

The above-described solvent is preferably the same as the solvent used in the aminomethylation step to be described later, particularly because it does not necessitates the drying step of the product, and specifically, selected from aqueous solvents such as water and alcohols.

In the fractional crystallization, first, dicyanocyclohexanes are dissolved in the above-described solvent, and the mixture is heated. Thereafter, the mixture is cooled to ambient temperature. This allows dicyanocyclohexanes having a high proportion of trans isomer to be crystallized (crystallization step). Thereafter, the crystallized dicyanocyclohexanes can be separated by filtration.

After the separation, as necessary, the mixture is washed and dried so that trans-dicyanocyclohexanes in a viscous liquid or in a solid state can be obtained.

When metal oxide is used as a catalyst in the above-described cyanation reaction, a metal component of the catalyst used may be contaminated in the obtained dicyanocyclohexanes as an impurity. The metal content is 3000 ppm or less, preferably 2000 ppm or less, and more preferably, 1500 ppm or less relative to dicyanocyclohexanes.

More than 3000 ppm metal contents are not preferable because resulting metal might inhibit the reaction in the aminomethylation step to be described later.

As necessary, the metal content is preferably reduced by various methods, for example, by a method in which catalyst removal operation such as filtration and adsorption after reaction are repeated; a method in which the solution of dicyanocyclohexanes before crystallization is brought into contact with activated carbon, synthetic adsorbent, etc. and then separated by filtration, and thereafter crystallized; and a method in which the dicyanocyclohexanes having a large amount of metal contents is re-dissolved in the above-described solvent, then brought into contact with activated carbon, synthetic adsorbent, etc. then separated by filtration, and thereafter, the solvent is distilled off.

Meanwhile, when stereoisomers of dicyanocyclohexanes are separated by fractional crystallization, in the filtrate after the crystallization and filtration, the dicyanocyclohexanes having a high cis isomer ratio is dissolved.

The dicyanocyclohexanes having a high cis isomer ratio obtained by distilling off the solvent from the filtrate are again fed into the reactor in the cyanation step, to be treated again with ammonia along with hydrogenated phthalic acids or phthalic acid derivatives.

In this manner, thermal isomerization occurs at a predetermined temperature in the reactor of the cyanation step to form an equilibrium composition mixture of cis isomer/trans isomer.

[Aminomethylation Step]

In the aminomethylation step, the dicyanocyclohexanes obtained in the cyanation step are treated with hydrogen, thereby producing bis(aminomethyl)cyclohexanes.

In the aminomethylation step, for example, the method described in, for example, Japanese Unexamined Patent Publication No. 2001-187765 can be used.

Quality of hydrogen used in the aminomethylation step is sufficient when the hydrogen is of industrial use, and the hydrogen may contain inactive gas (e.g., nitrogen, methane, etc.). The hydrogen concentration is preferably 50% or more.

As the hydrogenation catalyst used in the aminomethylation step, a known hydrogenation catalyst, for example, any of a cobalt catalyst, a nickel catalyst, a copper catalyst, and a noble metal catalyst can be used.

In view of reactivity and selectivity, a catalyst mainly composed of nickel, cobalt and/or ruthenium is preferably used, and more preferably, Raney catalyst or a catalyst supported on porous metal oxides such as silica, alumina, silica alumina, kieselguhr, and activated carbon is preferably used.

The catalyst may further contain metals such as aluminum, zinc, and silicon.

These hydrogenation catalysts may contain, as a reaction accelerator, a metal selected from chromium, iron, cobalt, manganese, tungsten, and molybdenum.

The hydrogenation catalyst can be used as a perfect solid catalyst, or can be used as a supported solid catalyst, for example, nickel, cobalt, or ruthenium supported on aluminum oxide, titanium oxide, zirconium oxide, magnesia/alumina, etc.

The catalyst is used in the form of, for example, powder, granular, or may be supported on a pellet carrier. Preferably, the catalyst is powder. When the catalyst has an appropriate size, for example, when the catalyst is powder catalyst, the catalyst contains an internal portion that effectively contributes to reaction in a large amount, and therefore the reaction rate does not easily decrease.

The amount of catalyst used is, in view of reactivity and selectivity, for example, 0.1 to 20 parts by weight, preferably 0.5 to 15 parts by weight relative to 100 parts by weight of dicyanocyclohexanes.

For the reaction, a solvent can be used suitably, and examples of such a solvent include aqueous solvents such as water; alcohols such as methanol, ethanol, 1-propanol, isopropanol, 1-butanol, 2-butanol, and t-butanol; and 1,4-dioxane.

The dicyanocyclohexanes concentration in the reaction solution is, for example, 1 to 50 wt %, preferably 2 to 40 wt %.

The dicyanocyclohexanes concentration in the reaction solution within such a range is advantageous in that the reaction rate does not decrease, and the temperature increase in the reactor is small.

The reaction is preferably performed in the presence of ammonia.

The ammonia works to suppress production of by-products such as secondary amine, tertiary amine, and polyamine, i.e., products other than the target bis(aminomethyl)cyclohexanes, that is, works to improve reaction selectivity.

The amount of ammonia used is, in view of suppressing production of the above-described by-products, preventing decrease in the hydrogenation rate, and making ammonia easy to treat or recover after reaction, for example, 0.05 to 5 mol, preferably 0.1 to 2.5 mol relative to 1 mol of dicyanocyclohexanes.

The reaction method is not particularly limited, and examples thereof include slurry-bed batch process, semi-batch process, and continuous process; and also fixed-bed continuous process. Preferably, liquid-phase slurry reaction is used.

The reactor is preferably a pressure-resistant vessel.

For example, dicyanocyclohexanes, catalyst, hydrogen, and as necessary a solvent and ammonia are introduced from the reactor top or bottom, and the mixture is allowed to react at a predetermined temperature.

The reaction pressure is usually 0.1 to 20 MPa, preferably 0.5 to 10 MPa, more preferably 0.5 to 8 MPa, and particularly preferably 0.5 to 5 MPa.

The reaction temperature is, in view of reactivity and selectivity, for example, 50 to 250° C., preferably 50 to 200° C., more preferably 70 to 150° C., and preferably, the reaction temperature is increased during the hydrogenation reaction continuously or stepwise.

After the reaction, bis(aminomethyl)cyclohexanes can be separated from the reaction mixture by a known method, for example, by filtration, distillation, etc.

The bis(aminomethyl)cyclohexanes obtained in the aminomethylation step have functional groups at substitution positions correlating with the ortho-, meta-, or para-form of the phthalic acids or phthalic acid derivatives used as the raw material, and are a mixture of cis isomer and trans isomer.

To be more specific, for example, when isophthalic acid or an isophthalic acid derivative is used as the raw material, bis(aminomethyl)cyclohexanes to be obtained is a mixture of 1,3-disubstituted cis isomer (that is, cis-1,3-bis(aminomethyl)cyclohexane) and 1,3-disubstituted trans isomer (that is, trans-1,3-bis(aminomethyl)cyclohexane); and for example, when terephthalic acid or a terephthalic acid derivative (para-phthalic acid) is used as the raw material, a mixture of 1,4-disubstituted cis isomer (that is, cis-1,4-bis(aminomethyl)cyclohexane) and 1,4-disubstituted trans isomer (that is, trans-1,4-bis(aminomethyl)cyclohexane).

Furthermore, for example, when isophthalic acid or an isophthalic acid derivative (meta-phthalic acid) and terephthalic acid or a terephthalic acid derivative (para-phthalic acid) are used in combination as the raw materials, the dicyanocyclohexanes to be obtained are a mixture of the above-described 1,3-disubstituted cis isomer, 1,3-disubstituted trans isomer, 1,4-disubstituted cis isomer, and 1,4-disubstituted trans isomer.

The method for producing bis(aminomethyl)cyclohexanes of the present invention is excellent in terms of equipment, safety, and economy, and achieves safe, low costs, and high yield production of bis(aminomethyl)cyclohexanes.

Thus, the method can be suitably used as an industrial method for producing bis(aminomethyl)cyclohexanes.

The above-described method for producing bis(aminomethyl)cyclohexanes includes the nuclear hydrogenation step, the cyanation step, and the aminomethylation step. However, in the method for producing bis(aminomethyl)cyclohexanes, for example, hydrogenated phthalic acids or phthalic acid derivatives are used as a starting material to omit the nuclear hydrogenation step, and the cyanation step and the aminomethylation step can be performed.

In such a case, the hydrogenated phthalic acids or phthalic acid derivatives as the starting material is not limited to the above-described hydrogenated phthalic acids or phthalic acid derivatives obtained in the nuclear hydrogenation step. However, with the above-described nuclear hydrogenation step, hydrogenated phthalic acids or phthalic acid derivatives can be obtained safely at low costs and with high yields, and therefore the hydrogenated phthalic acids or phthalic acid derivatives as a starting material is preferably obtained by the above-described nuclear hydrogenation step.

EXAMPLES

Hereinafter, the present invention will be described more specifically with reference to Examples. However, the present invention is not limited to those Examples. Analysis in the nuclear hydrogenation step was performed by high-performance liquid chromatography, and analyses in the cyanation step and the aminomethylation step were performed by gas chromatography. The metal component amount was analyzed by ICP (inductively coupled plasma) emission spectroscopy.

Example 1

Nuclear Hydrogenation Step

A 100 mL stainless steel-made autoclave equipped with a stirrer was charged with 25.0 g of terephthalic acid, 2.8 g of a catalyst (10% Pd/C, manufactured by NE Chemcat Corporation), and 100 mL of water. The autoclave was purged with nitrogen introduced from the autoclave nozzle inlet three times at 5 MPa, and the mixture was heated to 150° C. while stirring at 400 rpm under normal pressure.

When the temperature reached 150° C., hydrogen supply was started intermittently to achieve a pressure of 3.5 MPa, and the reaction was performed until there is no hydrogen absorption.

After the completion of reaction, the product was cooled to room temperature. The reaction mixture was taken out, and after a 5 N aqueous NaOH solution containing sodium hydroxide of 2.5 times mol the charged terephthalic acid amount was added thereto, the mixture was filtered to remove the catalyst.

The filtrate was neutralized with a 5N aqueous HCl solution, and then analyzed by high-performance liquid chromatography. It was found that the conversion of terephthalic acid was 100%, the yield of 1,4-cyclohexanedicarboxylic acid was 99%, and the trans isomer/cis isomer ratio was 33/67.

[Cyanation Step]

A four-neck flask equipped with a stirrer, a gas inlet tube, a thermometer, a gas purge line, and a condenser was charged with 9.3 g of 1,4-cyclohexanedicarboxylic acid obtained by concentrating the filtered reaction solution obtained in the nuclear hydrogenation step and 0.13 g of tin (II) oxide, and the mixture was heated to 170° C. while stirring at 300 rpm, thereby dissolving the carboxylic acid.

Thereafter, ammonia gas was introduced at a rate of 16 mL/min (0.81 mol equivalent/1,4-cyclohexanedicarboxylic acid/hr) to increase the temperature to 280° C., and while the temperature was kept constant, reaction was performed. After four hours, the reaction mixture was cooled to room temperature.

The solid product was suspended in methanol, and then the suspension was filtered to remove the catalyst.

The filtrate was analyzed by gas chromatography, and it was found that the conversion of 1,4-cyclohexanedicarboxylic acid was 99.5%, the yield of 1,4-dicyanocyclohexane was 94.7%, and the trans isomer/cis isomer ratio was 58/42.

Next, to 8 g of 1,4-dicyanocyclohexane containing a mixture of the trans isomer and the cis isomer obtained by distilling off the solvent from the filtrate obtained as described above, 18.7 g of 1-butanol was added, and heated to 80° C. to dissolve the 1,4-dicyanocyclohexane. Thereafter, as the mixture was cooled to room temperature, a precipitant was appeared.

The suspension liquid was filtered, and the residue was further washed with 18.7 g of 1-butanol. Thereafter, the residue was dried, and 3.8 g of white solid was obtained (yield 48%).

The obtained white solid was analyzed by gas chromatography, and it was found that the solid was 1,4-dicyanocyclohexane having a purity of 99.5% or more, and the trans isomer/cis isomer ratio was 94/6.

A metal (tin) content of the solid was 10 ppm or less, which is 9.95 (10×0.995) ppm or less relative to dicyanocyclohexane (including trans isomer and cis isomer).

Meanwhile, the solvent was distilled off from the filtrate after the filtration, and 4.2 g of a yellow solid was obtained. The obtained yellow solid was analyzed by gas chromatography, and it was found that the solid was 1,4-dicyanocyclohexane having a purity of 87%, and the trans isomer/cis isomer ratio was 16/84.

[Aminomethylation Step]

A 100 mL stainless steel-made autoclave equipped with a stirrer was charged with 3.5 g of 1,4-dicyanocyclohexane having a trans isomer/cis isomer ratio of 94/6 obtained in the cyanation step, 0.35 g of a catalyst (manganese-containing Raney cobalt manufactured by Kawaken Fine Chemicals Co., Ltd.), 3.9 mL of a 28 wt % ammonia water, and 7.3 mL of 1-butanol. The autoclave was purged with nitrogen introduced from the autoclave nozzle inlet three times at 2 MPa, and the mixture was heated to 80° C. while stirring at 400 rpm.

When the temperature reached 80° C., hydrogen supply was started intermittently to achieve a pressure of 0.95 MPa, and the reaction was performed until there is no hydrogen absorption.

After the completion of reaction, the product was cooled to room temperature. The reaction mixture was taken out, and the mixture was filtered to remove the catalyst.

The filtrate was analyzed by gas chromatography, and it was found that the conversion of 1,4-dicyanocyclohexane was 100%, the yield of 1,4-bis(aminomethyl)cyclohexane was 96%, and the trans isomer/cis isomer ratio was 87/13.

The filtrate was distilled under a reduced pressure of 10 mmHg, and 1,4-bis(aminomethyl)cyclohexane having a purity of 99.5% or more and a trans isomer/cis isomer ratio of 88/12 was obtained with a yield of 97%.

Example 2

Nuclear Hydrogenation Step

A 100 mL stainless steel-made autoclave equipped with a stirrer was charged with 25.1 g of isophthalic acid, 2.8 g of a catalyst (10% Pd/C, manufactured by NE Chemcat Corporation), and 100 mL of water. The autoclave was purged with nitrogen introduced from the autoclave nozzle inlet three times at 5 MPa, and the mixture was heated to 150° C. while stirring at 400 rpm under normal pressure.

When the temperature reached 150° C., hydrogen supply was started intermittently to achieve a pressure of 3.5 MPa, and the reaction was performed until there is no hydrogen absorption.

After the completion of reaction, the product was cooled to room temperature. The reaction mixture was taken out, and after a 5N aqueous NaOH solution containing sodium hydroxide of 2.5 times mol the charged isophthalic acid amount was added thereto, the mixture was filtered to remove the catalyst.

The filtrate was neutralized with a 5N aqueous HCl solution, and then analyzed by high-performance liquid chromatography. It was found that the conversion of isophthalic acid was 100%, and the yield of 1,3-cyclohexanedicarboxylic acid was 99%.

[Cyanation Step]

A four-neck flask equipped with a stirrer, a gas inlet tube, a thermometer, a gas purge line, and a condenser was charged with 9.1 g of 1,3-cyclohexanedicarboxylic acid obtained by filtering and concentrating the reaction solution obtained in the nuclear hydrogenation step and 0.12 g of tin (II) oxide, and the mixture was heated to 170° C. while stirring at 300 rpm, thereby dissolving the carboxylic acid.

Thereafter, ammonia gas was introduced at a rate of 16 mL/min (0.81 mol equivalent/1,3-cyclohexanedicarboxylic acid/hr) to increase the temperature to 280° C., and while the temperature was kept constant, reaction was performed. After four hours, the reaction mixture was cooled to room temperature.

The solid product was suspended in methanol, and then the suspension was filtered to remove the catalyst.

The filtrate was analyzed by gas chromatography, and it was found that the conversion of 1,3-cyclohexanedicarboxylic acid was 98.5%, the yield of 1,3-dicyanocyclohexane was 94.7%, and the trans isomer/cis isomer ratio was 45/55.

Then, the solvent was distilled off from the filtrate obtained as described above and the filtrate was dried, thereby producing 7.8 g of a yellow solid.

The yellow solid was analyzed by gas chromatography, and it was found that solid was 1,3-dicyanocyclohexane having a purity of 95.3%.

A metal (tin) content of the solid was 10 ppm or less, which was 9.53 (10×0.953) ppm or less relative to dicyanocyclohexane (including trans isomer and cis isomer).

[Aminomethylation Step]

A 100 mL stainless steel-made autoclave equipped with a stirrer was charged with 3.5 g (3.7 g of yellow solid) of 1,3-dicyanocyclohexane having a trans isomer/cis isomer ratio of 45/55 obtained in the cyanation step, 0.35 g of a catalyst (manganese-containing Raney cobalt manufactured by Kawaken Fine Chemicals Co., Ltd.), 3.9 mL of a 28 wt % ammonia water, and 7.3 mL of 1-butanol. The autoclave was purged with nitrogen introduced from the autoclave nozzle inlet three times at 2 MPa, and the mixture was heated to 80° C. while stirring at 400 rpm under normal pressure.

When the temperature reached 80° C., hydrogen supply was started intermittently to achieve a pressure of 0.95 MPa, and the reaction was performed until there is no hydrogen absorption.

After the completion of reaction, the mixture was cooled to room temperature. The reaction mixture was taken out, and the mixture was filtered to remove the catalyst.

The filtrate was analyzed by gas chromatography, and it was found that the conversion of 1,3-dicyanocyclohexane was 100%, the yield of 1,3-bis(aminomethyl)cyclohexane was 94%, and the trans isomer/cis isomer ratio was 42/58.

The filtrate was distilled under a reduced-pressure of 10 mmHg, and 3-bis(aminomethyl)cyclohexane having a purity of 99.5% or more was obtained with a yield of 97%.

Example 3

A four-neck flask equipped with a stirrer, a gas inlet tube, a thermometer, a gas purge line, and a condenser was charged with 15.1 g of 1,4-cyclohexanedicarboxylic acid, 17.4 g of dimethyl 1,4-cyclohexanedicarboxylate, 4.9 g of N,N'-dimethylimidazolidinone (boiling point 226° C.), and 0.40 g of tin (II) oxide, and the mixture was heated to 210° C. while stirring at 250 rpm.

Thereafter, ammonia gas was introduced at a rate of 72 mL/min (1.1 mol equivalent/1,4-cyclohexanedicarboxylic acid+dimethyl 1,4-cyclohexanedicarboxylate/hr). The temperature inside the reactor was kept at 210° C. for 1 hour, and then thereafter, increased to 280° C.: while the temperature was kept constant, reaction was performed. After 8 hours, the reaction mixture was cooled to 90° C. When the reaction was terminated, almost no white solid was observed in the gas purge line and the condenser.

Then, 31.6 g of 1-butanol was added thereto and the mixture was stirred to produce a reaction mixture. The reaction mixture was filtered by hot filtration to remove the catalyst. The filtrate was analyzed by gas chromatography, and it was found that the conversion of 1,4-cyclohexanedicarboxylic acid was 100%, the conversion of dimethyl 1,4-cyclohexanedicarboxylate was 99.9%, the yield of 1,4-dicyanocyclohexane was 89%, and the trans isomer/cis isomer ratio was 53/47.

Next, 12.6 g of 1-butanol was added to 37.3 g of the filtrate obtained as described above at 90° C., and as the mixture was cooled while stirring to room temperature, a precipitant was appeared. The suspension liquid was filtered, and the residue was further washed twice with 17.5 g of 1-butanol. Thereafter, the residue was dried, thereby producing 6.7 g of a light yellow solid (yield 45%).

The obtained light yellow solid was analyzed by gas chromatography, and it was found that the solid was 1,4-dicyanocyclohexane having a purity of 99.5% or more, and the trans isomer/cis isomer ratio was 95/5.

A metal (tin) content of the solid was 1 ppm or less, which is 0.995 (1×0.995) ppm or less relative to 1,4-dicyanocyclohexane (including trans isomer and cis isomer) and 0.945 (0.995×0.95) ppm or less relative to trans-1,4-dicyanocyclohexane.

Meanwhile, the solvent was distilled off from the filtrate after the filtration and washings, and 7.0 g of a yellow solid was obtained. The obtained yellow solid was analyzed by gas chromatography, and it was found that the solid was 1,4-dicyanocyclohexane having a purity of 89%, and the trans isomer/cis isomer ratio was 13/87.

Example 4

13.5 g of a yellow solid obtained in the same manner as in Example 3 (12.0 g of 1,4-dicyanocyclohexane) was added to the reactor in the cyanation step, and reaction was performed in the same manner as in Example 3, except that dimethyl 1,4-cyclohexanedicarboxylate was not added, and the rate of the ammonia gas introduction was changed to 36 mL/min (1.1 mol equivalent/1,4-cyclohexanedicarboxylic acid/hr).

After 15 hours, the reaction mixture was treated in the same manner as in Example 3.

As a result of gas chromatography analysis, it was found that the conversion of 1,4-cyclohexanedicarboxylic acid was 100%, the yield of 1,4-dicyanocyclohexane was 94.5%, and the trans isomer/cis isomer ratio was 53/47. The cyanation reaction proceeded with high yields even if the recovered solid mainly composed of the separated cis-1,4-dicyanocyclohexane was fed again to be used in the cyanation step.

Example 5

A four-neck flask equipped with a stirrer, a gas inlet tube, a thermometer, a gas purge line, and a condenser was charged with 15.1 g of 1,3-cyclohexanedicarboxylic acid obtained in the same manner as in Example 2, 17.4 g of dimethyl 1,3-cyclohexanedicarboxylate, 5.0 g of N,N'-dimethylimidazolidinone (boiling point 226° C.), and 0.40 g of tin (II) oxide, and the mixture was heated to 210° C. while stirring at 250 rpm.

Thereafter, ammonia gas was introduced at a rate of 72 mL/min (1.1 mol equivalent/1,3-cyclohexanedicarboxylic acid+dimethyl 1,3-cyclohexanedicarboxylate/hr). The temperature inside the reactor was kept at 210° C. for 1 hour, and then thereafter, increased to 280° C.: while the temperature was kept constant, reaction was performed. After 8 hours, the reaction was terminated, and the reaction product was cooled to 90° C. When the reaction was terminated, almost no white solid was observed in the gas purge line and the condenser.

Then, 31.6 g of 1-butanol was added thereto and the mixture was stirred to produce a reaction mixture. The reaction mixture was filtered by hot filtration to remove the catalyst. The filtrate was analyzed by gas chromatography, and it was found that the conversion of 1,3-cyclohexanedicarboxylic acid was 100%, the conversion of dimethyl 1,4-cyclohexanedicarboxylate was 99%, the yield of 1,3-dicyanocyclohexane was 86%, and the trans isomer/cis isomer ratio was 47/53.

Then, the solvent was distilled off from the filtrate obtained as described above and the filtrate was dried, thereby producing a yellow solid. The yellow solid was analyzed by gas chromatography, and it was found that solid was 1,3-dicyanocyclohexane having a purity of 96.1%.

A metal (tin) content of the solid was 10 ppm or less, which was 9.61 (10×0.961) ppm or less relative to 1,3-dicyanocyclohexane (including trans isomer and cis isomer).

Example 6

Cyanation Step

A four-neck flask equipped with a stirrer, a gas inlet tube, a thermometer, a gas purge line, and a condenser was charged with 75.3 g of 1,3-cyclohexanedicarboxylic acid, 15.1 g of N,N'-dimethylimidazolidinone, and 0.95 g of tin (II) oxide, and the mixture was heated to 210° C. while stirring at 300 rpm.

Thereafter, ammonia gas and nitrogen gas were mixedly introduced at a rate of 135 mL/min (0.83 mol equivalent/1,3-cyclohexanedicarboxylic acid/hr) and a rate of 15 mL/min, respectively. The temperature was increased to 280° C., and while the temperature was kept constant, reaction was performed. After 35 hours, the reaction mixture was cooled to 90° C. When the reaction was terminated, almost no white solid was observed in the gas purge line and the condenser.

70 g of 1-butanol was added to 30 g of the reaction mixture and stirred. The reaction mixture was filtered by hot filtration to remove the catalyst. The filtrate was analyzed by gas chromatography, and it was found that the conversion of 1,3-cyclohexanedicarboxylic acid was 100%, the yield of 1,3-dicyanocyclohexane was 90%, and the trans isomer/cis isomer ratio was 59/41.

The remaining of the mixture was filtered by hot filtration in the same manner as described above to separate the catalyst. The solvent was distilled off therefrom together with the filtrate for 30 g of the mixture that previously underwent hot filtration, thereby producing 58 g of a yellow viscous liquid. The viscous liquid had a purity of 96%, and a metal (tin) content of 10 ppm or less, which was 9.6 (10×0.96) ppm or less relative to 1,3-dicyanocyclohexane (including trans isomer and cis isomer).

30 g of the viscous liquid was distilled under a reduced-pressure of 5 mmHg, thereby producing 25 g of a colorless semi-solid. The semi-solid was analyzed by gas chromatography, and it was found that 1,3-dicyanocyclohexane had a purity of 99.5% or more, and its trans isomer/cis isomer ratio was 67/33. A metal (tin) content of the semi-solid was 1 ppm or less, which was 0.995 (1×0.995) ppm or less relative to 1,3-dicyanocyclohexane (including trans isomer and cis isomer).

[Aminomethylation Step]

A 100 mL stainless steel-made autoclave equipped with a stirrer was charged with 10.0 g of 1,3-dicyanocyclohexane having a trans isomer/cis isomer ratio of 59/41 (10.4 g of yellow viscous liquid), i.e., a yellow viscous solid before the distillation obtained in the above-described cyanation step, 0.48 g of a catalyst (manganese-containing Raney cobalt manufactured by Kawaken Fine Chemicals Co., Ltd.), 9.6 g of a 28 wt % ammonia water, and 11.4 g of 1-butanol. The autoclave was purged with nitrogen introduced from the autoclave nozzle inlet three times at 5 MPa, and the mixture was heated to 80° C. while stirring at 400 rpm under normal pressure.

When the temperature reached 80° C., hydrogen supply was started continuously to achieve a pressure of 3.5 MPa, and the reaction was performed under a constant pressure until there is no hydrogen absorption. The reaction time was 5.2 hours.

After the completion of reaction, the mixture was cooled to room temperature. The reaction mixture was taken out, and the mixture was filtered to remove the catalyst.

The filtrate was analyzed by gas chromatography, and it was found that the conversion of 1,3-dicyanocyclohexane was 100%, the yield of 1,3-bis(aminomethyl)cyclohexane was 93%, and the trans isomer/cis isomer ratio was 59/41.

The filtrate was distilled under a reduced-pressure of 5 mmHg, and 1,3-bis(aminomethyl)cyclohexane having a purity of 99.5% or more was obtained with a yield of 91%.

Example 7

A 100 mL stainless steel-made autoclave equipped with a stirrer was charged with 9.1 g of 1,3-dicyanocyclohexane having a trans isomer/cis isomer ratio of 67/33 (9.1 g of colorless semi-solid), i.e., a colorless semi-solid after the distillation obtained in the cyanation step of Example 6, 0.46 g of a catalyst (manganese-containing Raney cobalt manufactured by Kawaken Fine Chemicals Co., Ltd.), 9.7 g of a 28 wt % ammonia water, and 11.4 g of 1-butanol. The autoclave was purged with nitrogen introduced from the autoclave nozzle inlet three times at 5 MPa, and the mixture was heated to 80° C. while stirring at 400 rpm under normal pressure.

When the temperature reached 80° C., hydrogen supply was started continuously to achieve a pressure of 3.5 MPa, and the reaction was performed under a constant pressure until there is no hydrogen absorption. The reaction time was 4.4 hours.

After the completion of reaction, the mixture was cooled to room temperature. The reaction mixture was taken out, and was filtered to remove the catalyst.

The filtrate was analyzed by gas chromatography, and it was found that the conversion of 1,3-dicyanocyclohexane was 100%, the yield of 1,3-bis(aminomethyl)cyclohexane was 93%, and the trans isomer/cis isomer ratio was 67/33.

The filtrate was distilled under a reduced-pressure of 5 mmHg, and 1,3-bis(aminomethyl)cyclohexane having a purity of 99.5% or more was obtained with a yield of 90%.

While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY

The present invention allows for an industrially advantageous production of bis(aminomethyl)cyclohexanes using a raw material cheaper than conventional ones: the raw material such as phthalic acids or phthalic acid derivatives of at least one selected from the group consisting of phthalic acids, phthalic acid esters, and phthalic acid amides.

The compound is used suitably for polyimide, polyimide, polyurethane, and polyisocyanate, and also for a curing agent of epoxy resins.

The invention claimed is:

1. A method for producing bis(aminomethyl)cyclohexanes, the method comprising:
   a nuclear hydrogenation step of producing hydrogenated phthalic acids or phthalic acid derivatives by nuclear hydrogenation of phthalic acids or phthalic acid derivatives of at least one selected from the group consisting of phthalic acids, phthalic acid esters, and phthalic acid amides,
   a cyanation step of treating the hydrogenated phthalic acids or phthalic acid derivatives obtained in the nuclear hydrogenation step with ammonia, wherein in the cyanation step, the reaction with ammonia is performed in the presence of a solvent having a boiling point of 180° C. to 350° C., thereby producing dicyanocyclohexanes, and
   an aminomethylation step of treating the dicyanocyclohexanes obtained in the cyanation step with hydrogen, thereby producing bis(aminomethyl)cyclohexanes,
   wherein metal oxide is used as a catalyst in the cyanation step, and the obtained dicyanocyclohexanes have a metal content of 3000 ppm or less.

2. A method for producing bis(aminomethyl)cyclohexanes, the method comprising:
   a cyanation step of treating hydrogenated phthalic acids or phthalic acid derivatives with ammonia, thereby producing dicyanocyclohexanes, wherein in the cyanation step, the reaction with ammonia is performed in the presence of a solvent having a boiling point of 180° C. to 350° C., and
   an aminomethylation step of treating the dicyanocyclohexanes obtained in the cyanation step with hydrogen, thereby producing bis(aminomethyl)cyclohexanes,
   wherein metal oxide is used as a catalyst in the cyanation step, and the obtained dicyanocyclohexanes have a metal content of 3000 ppm or less.

3. The method for producing bis(aminomethyl)cyclohexanes according to claim 2, wherein
   the hydrogenated phthalic acids or phthalic acid derivatives are obtained by
   a nuclear hydrogenation step of nuclear hydrogenation of phthalic acids or phthalic acid derivatives of at least one selected from the group consisting of phthalic acids, phthalic acid esters, and phthalic acid amides.

4. The method for producing bis(aminomethyl)cyclohexanes according to claim 1, wherein
   in the cyanation step, the ammonia to be brought into contact with is fed at a rate greater than 0.5 mol equivalent/hydrogenated phthalic acids or phthalic acid derivatives/hr.

5. The method for producing bis(aminomethyl)cyclohexanes according to claim 1, wherein
   in the cyanation step, the reaction with ammonia is performed in the presence of 3 to 20 parts by weight of a solvent relative to 100 parts by weight of the hydrogenated phthalic acids or phthalic acid derivatives.

6. The method for producing bis(aminomethyl)cyclohexanes according to claim 1, wherein
   a solvent is used in the cyanation step, the solvent being selected from o-dichlorobenzene, triethylene glycol dimethylether, tetraethylene glycol dimethylether, N-methyl-2-pyrrolidinone, N,N'-dimethylimidazolidinone, N,N'-diethylimidazolidinone, N,N'-dipropylimidazolidinone, N,N',4-trimethylimidazolidinone, and N,N'-dimethylpropyleneurea.

7. The method for producing bis(aminomethyl)cyclohexanes according to claim 2, wherein
   in the cyanation step, the ammonia to be brought into contact with is fed at a rate greater than 0.5 mol equivalent/hydrogenated phthalic acids or phthalic acid derivatives/hr.

8. The method for producing bis(aminomethyl)cyclohexanes according to claim 2, wherein
   in the cyanation step, the reaction with ammonia is performed in the presence of 3 to 20 parts by weight of a solvent relative to 100 parts by weight of the hydrogenated phthalic acids or phthalic acid derivatives.

9. The method for producing bis(aminomethyl)cyclohexanes according to claim 2, wherein
   a solvent is used in the cyanation step, the solvent being selected from o-dichlorobenzene, triethylene glycol dimethylether, tetraethylene glycol dimethylether, N-methyl-2-pyrrolidinone, N,N'-dimethylimidazolidinone, N,N'-diethylimidazolidinone, N,N'-dipropylimidazolidinone, N,N',4-trimethylimidazolidinone, and N,N'-dimethylpropyleneurea.

* * * * *